(12) United States Patent
Rasmussen et al.

(10) Patent No.: US 8,033,047 B2
(45) Date of Patent: Oct. 11, 2011

(54) ALGAE CULTIVATION SYSTEMS AND METHODS

(75) Inventors: Mark Axel Rasmussen, Anoka, MN (US); Clayton V. McNeff, Andover, MN (US); Larry C. McNeff, Anoka, MN (US)

(73) Assignee: Sartec Corporation, Anoka, MN (US)

( * ) Notice: Subject to any disclaimer, the term of this patent is extended or adjusted under 35 U.S.C. 154(b) by 204 days.

(21) Appl. No.: 12/257,008

(22) Filed: Oct. 23, 2008

(65) Prior Publication Data

US 2009/0126265 A1 May 21, 2009

Related U.S. Application Data

(60) Provisional application No. 60/982,007, filed on Oct. 23, 2007.

(51) Int. Cl.
*A01H 13/00* (2006.01)
(52) U.S. Cl. .......................... 47/1.4; 435/292.1
(58) Field of Classification Search ............... 47/1.4; 435/292.1; *A01H 13/00*
See application file for complete search history.

(56) References Cited

U.S. PATENT DOCUMENTS

| | | | | |
|---|---|---|---|---|
| 4,236,349 A | * | 12/1980 | Ramus | 47/1.4 |
| 5,104,803 A | * | 4/1992 | Delente | 435/292.1 |
| 5,151,347 A | * | 9/1992 | Delente et al. | 435/3 |
| 6,083,740 A | | 7/2000 | Kodo et al. | |
| 6,602,703 B2 | * | 8/2003 | Dutil | 435/292.1 |
| 2003/0059932 A1 | * | 3/2003 | Craigie et al. | 435/292.1 |
| 2003/0073231 A1 | * | 4/2003 | Dutil | 435/292.1 |
| 2005/0239197 A1 | * | 10/2005 | Katerkamp et al. | 435/292.1 |
| 2007/0289206 A1 | | 12/2007 | Kertz | |
| 2008/0155890 A1 | * | 7/2008 | Oyler | 47/1.4 |

(Continued)

FOREIGN PATENT DOCUMENTS

WO  WO-2007147028  12/2007

OTHER PUBLICATIONS

Abeliovich, Aharon et al., "Role of Heterotrophic Nutrition in Growth of the Alga Scenedesmus obliquus in High-Rate Oxidation Ponds", *Applied and Environmental Microbiology* Jan. 1978, vol. 35, No. 1, pp. 32-37.

(Continued)

*Primary Examiner* — Rob Swiatek
*Assistant Examiner* — Kristen Hayes
(74) *Attorney, Agent, or Firm* — Pauly, DeVries Smith & Deffner, L.L.C.

(57) ABSTRACT

An algae cultivation system and method. In an embodiment, an algae cultivation system is included. The algae cultivation system can include a cultivation tank, a plurality of light transmitting elements configured to be at least partially submerged in a liquid medium disposed within the cultivation tank, wherein the light transmitting elements increase the effective surface area of the liquid medium exposed to light, and a plurality of gas injectors configured to emit gas into the liquid medium. In an embodiment a method of culturing algae is included. The method can include measuring the amount of carbon dioxide in a cultivation system and modulating the amount of light being supplied to the cultivation system based on the measured amount of carbon dioxide. In an embodiment, a method of culturing algae can include measuring the amount of light being input into a cultivation system and modulating the amount of carbon dioxide being supplied to the cultivation system based on the measured amount of light. Other embodiments are also described herein.

14 Claims, 11 Drawing Sheets

U.S. PATENT DOCUMENTS

| | | | | |
|---|---|---|---|---|
| 2008/0220515 | A1* | 9/2008 | McCall | 435/292.1 |
| 2009/0029445 | A1 | 1/2009 | Eckelberry et al. | |
| 2010/0167381 | A1* | 7/2010 | Woerlee et al. | 435/257.1 |

OTHER PUBLICATIONS

Stepan, Daniel J. et al., "Carbon Dioxide Sequestering Using Microalgal Systems", *U.S. Department of Energy Report 2002-EERC-02-03* Feb. 2002, pp. 1-32.

Miao, Xiaoling et al., "Biodiesel Production from Heterotrophic Microalgal Oil", *Bioresource Technology* Apr. 2005, vol. 97, Issue 6, pp. 841-846 (Abstract Only).

Chisti, Yusuf, "Biodiesel from microalgae", *Biotechnology Advances 25* 2007, 25, pp. 294-306.

Greque De Morais, Michele et al., "Isolation and selection of microalgae from coal fired thermoelectric power plant for biofixation of carbon dioxide", *Energy Conversion and Management* 2007, vol. 48, No. 7, pp. 2169-2173 (Abstract Only).

Carvalho, Ana P. et al., "Microalgal reactors: A review of enclosed system designs and performances", *Biotechnology progress* 2006, vol. 22, No. 6, pp. 1490-1506 (Abstract Only).

Marxen, Kai et al., "A Photobioreactor System for Computer Controlled Cultivation of Microalgae", *Journal of Applied Phycology* 2005, vol. 17, No. 6, pp. 535-549 (Abstract Only).

Vunjak-Novakovic, Gordana et al., "Air-Lift Bioreactors for Algal Growth on Flue Gas: Mathematical Modeling and Pilot-Plant Studies", *Industrial & Engineering Chemistry Research* 2005, vol. 44, No. 16, pp. 6154-6163 (Abstract Only).

Doucha, Jiri et al., "Utilization of flue gas for cultivation of microalgae (*Chlorella* sp.) in an outdoor open thin-layer photobioreactor", *Journal of Applied Phycology* 2005, vol. 17, No. 5, pp. 403-412 (Abstract Only).

Jeong, Mijeong L. et al., "Carbon Dioxide Mitigation by Microalgal Photosynthesis", *Bull. Korean Chem. Soc.* 2003, vol. 24, No. 12, 1763-1766.

Barbosa, Maria J. et al., "Microalgae cultivation in air-lift reactors: Modeling biomass yield and growth rate as a function of mixing frequency", *Biotechnology and Bioengineering* 2003, vol. 82, No. 2, pp. 170-179 (Abstract Only).

Kremer, G. et al., "Practical Photosynthetic Carbon Dioxide Mitigation", www.ent.ohiou.edu/~ohiocoal/projects/algae.pdf 2002, pp. 1-6.

Bayless, David J. et al., "Final Technical Report: Carbon Dioxide Mitigation through Controlled Photosynthesis", *Department of Mechanical Engineering* Nov. 14, 2000, pp. 1-32.

* cited by examiner

ALGAE CULTIVATION SYSTEMS AND METHODS

This application claims the benefit of U.S. Provisional Application No. 60/982,007, filed Oct. 23, 2007, the content of which is herein incorporated by reference in its entirety.

FIELD OF THE INVENTION

The present invention relates to algae cultivation systems and methods.

BACKGROUND OF THE INVENTION

The global carbon cycle is heavily influenced by the activities of man. For example, the combustion of fuels by man is believed to have resulted in a large increase in the amount of carbon dioxide present in the atmosphere. In the last hundred years, global fossil carbon emissions have increased by more than a factor of ten. As nations around the globe continue to become more industrialized, demands for energy are expected to increase dramatically. As such, in the absence of new technological solutions, it is believed that the trend toward increased fossil carbon emissions will continue.

Carbon dioxide is considered to be a "greenhouse" gas and is believed to have contributed to global warming trends. Carbon dioxide, along with water vapor, methane, nitrous oxide, and ozone, causes more heat to be retained by the Earth than would otherwise be captured. The global average air temperature near the Earth's surface rose $0.74 \pm 0.18°$ C. during the last 100 years. It is believed that this is due, at least in part, to the observed increase in greenhouse gas concentrations. Further increases in global temperatures may lead to various catastrophic effects including a rising sea level, increased extreme weather events, reduced agricultural yields, glacier retreat, and species extinction, amongst others.

In an effort to prevent catastrophic events from occurring, significant resources have been devoted to developing systems to reduce the amount of carbon dioxide emitted into the atmosphere. The various strategies pursued can be grouped into two broad categories: reduction of carbon emissions and capture of atmospheric carbon.

In nature, plants efficiently capture atmospheric carbon through the process of photosynthesis. Using sunlight as energy, plants convert carbon dioxide and water into the precursors of carbohydrates and other plant constituents. Many different types of plants and microorganisms capture considerable amounts of carbon dioxide. Algae are photosynthetic organisms that occur in most habitats. They vary from small, single-celled forms to complex multicellular forms. Algae are estimated to generate as much as 80 percent of the Earth's oxygen. It is also estimated that algae fix 90 gigatons of carbon per year.

Various attempts have been made at designing algae culture systems in order to capture carbon dioxide. In general, there are two types of algae culture systems: open culture systems and closed culture systems. Open culture systems are open to the atmosphere. They have the advantage of being relatively inexpensive to construct. However, open culture systems are subject to atmospheric temperature fluctuations, are susceptible to contamination issues, and suffer substantial losses of water due to evaporation. In contrast, closed culture systems are closed to the atmosphere and therefore provide the advantages of a controlled environment, lower evaporative water loss, and fewer contamination issues. However, many closed culture systems require relatively complex structures and therefore have substantially higher construction and operating costs. In addition, many closed culture systems have issues associated with insufficient light penetration, algae growth on walls that can be difficult to clean, and poor temperature control.

For at least these reasons, a need remains for algae cultivation systems and methods.

SUMMARY OF THE INVENTION

Embodiments of the present invention relate to algae cultivation systems and methods. In an embodiment, an algae cultivation system is included. The algae cultivation system can include a cultivation tank, a plurality of light transmitting elements configured to be at least partially submerged in a liquid medium disposed within the cultivation tank, wherein the light transmitting elements increase the effective surface area of the liquid medium exposed to light, and a plurality of gas injectors configured to emit gas into the liquid medium.

In an embodiment a method of culturing algae is included. The method can include measuring the amount of carbon dioxide in a cultivation system and modulating the amount of light being supplied to the cultivation system based on the measured amount of carbon dioxide.

In an embodiment, a method of culturing algae can include measuring the amount of light input into a cultivation system and modulating the amount of carbon dioxide being supplied to the cultivation system based on the measured amount of light.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail.

It should be understood; however, that the invention is not limited to the particular embodiments described. On the contrary, the intention is to cover modifications, equivalents, and alternatives falling within the spirit and scope of the invention.

DETAILED DESCRIPTION OF THE INVENTION

Included herein are systems and methods for culturing algae. In an embodiment an algae cultivation system is provided that can include a cultivation tank, a liquid medium disposed within the cultivation tank, a plurality of light transmitting elements submerged in the liquid medium, and a plurality of gas injectors. The light transmitting elements can be configured to increase the effective surface area of the liquid medium exposed to light, thereby increasing the ratio of illuminated surface area to total volume of the cultivation system. It is believed that increasing this ratio can contribute to enhancing the overall productivity of the cultivation system. Light transmitting elements used with embodiments of the invention can be relatively simple in design and easy to clean, making the system more cost effective than many typical closed culture systems. As such, various embodiments of algae cultivation systems described herein can combine advantages normally associated with closed culture systems, such as high productivity per unit volume, with advantages normally associated with open culture systems, such as relatively low construction and operating costs. Various aspects of exemplary embodiments will now be described in greater detail.

Figure 1:
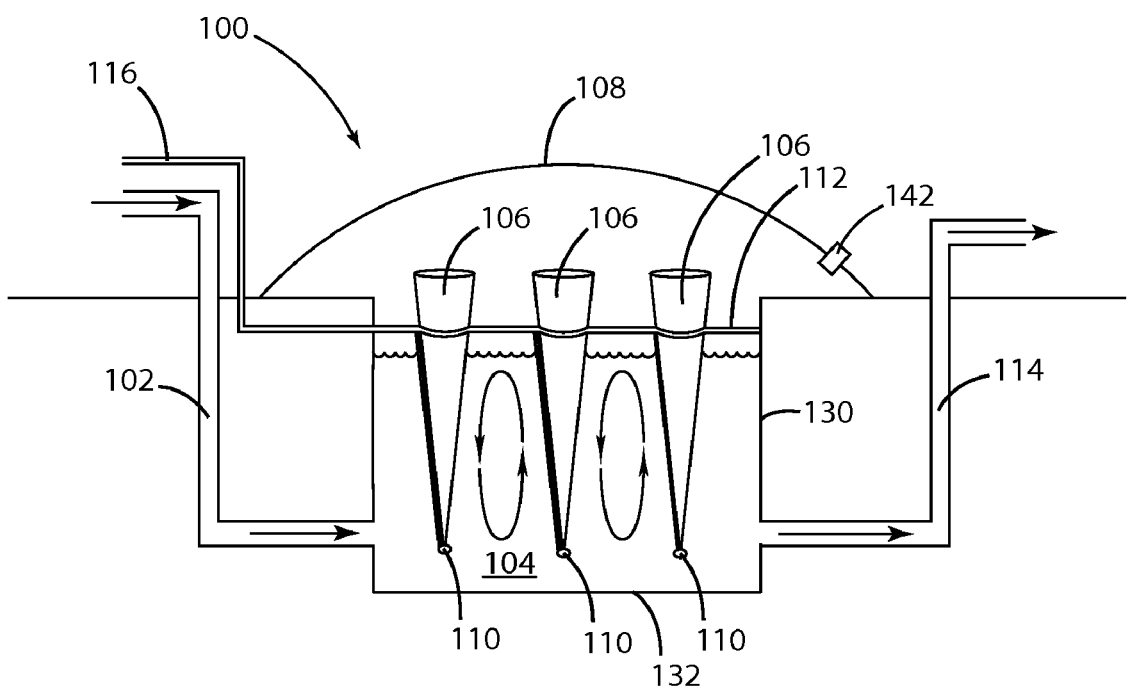
FIG. 1 is a schematic diagram of an algae cultivation system in accordance with an embodiment.

Referring now to FIG. 1, a schematic diagram of an algae cultivation system 100 in accordance with an embodiment is shown. The algae cultivation system 100 includes a cultivation tank 104. The cultivation tank 104 can be filled with a liquid medium that includes algae. Sunlight can pass through a cover 108 and into the cultivation tank 104.

While not intending to be bound by theory, it is believed that the intensity of algae growth is impacted by the ratio of the effective surface area of the liquid medium inside of the cultivation tank 104 to the total volume of the liquid medium inside of the cultivation tank 104. In general, the larger the effective surface area across which light can enter the algae containing medium (or "illuminated surface area"), the more productive the cultivation system can become. This is because light can only penetrate into a liquid containing a substantial amount of algae a relatively short distance before it is significantly attenuated.

In the embodiment of FIG. 1, the illuminated surface area is increased by the presence of a plurality of light transmitting elements 106. The light transmitting elements 106 can extend into the liquid medium inside of the cultivation tank 104. The body of the light transmitting elements 106 can serve to transmit light. As such, the area of the liquid medium in the cultivation tank touching the light transmitting elements 106 effectively becomes additional surface area. Therefore, the illuminated surface area per unit volume in the cultivation tank 104 is substantially increased by the presence of the light transmitting elements 106. Various aspects of exemplary light transmitting elements 106 will be described in greater detail below.

The light transmitting elements 106 can be held in place with a frame 112. In some embodiments, the frame 112 can be moved with respect to the cultivation tank 104. By way of example, it may be desirable to periodically clean the light transmitting elements 106. In this case the frame 112 can be moved in order to lift the light transmitting elements 106 out of the liquid medium within the cultivation tank 104.

The cover 108 can be configured to prevent evaporation, regulate gas transfer, retain heat, modulate light transmittance and prevent contaminant materials from entering the cultivation tank 104 from the outside. In some embodiments, the cover 108 has a hemispherical shape. In other embodiments, the cover can be relatively flat. The cover can be made from a polymer, a glass, or crystal. In some cases the cover 108 can include multiple layers of material, with or without space in between the layers. In some embodiments, the cover can be removable to enable convenient access to the cultivation tank 104.

The cultivation tank 104 can have various dimensions, depending on the desired capacity of the algae cultivation system 100. In some embodiments the depth of the cultivation tank 104 can be greater than about one foot. In some embodiments, the depth of the cultivation tank 104 can be greater than about three feet. In some embodiments, the depth of the cultivation tank 104 can be greater than about five feet.

The cultivation tank 104 can include walls such as side walls 130 and a bottom 132. In some embodiments, the side walls 130 are perpendicular to the bottom 132. In some embodiments, the intersection between the side walls 130 and the bottom 132 can be at a sharp angle, such as a sharp ninety degree angle. However, in other embodiments, the intersection between the side walls 130 and the bottom 132 can be a smooth curved junction.

Additional liquid can flow into the cultivation tank 104 through an ingress conduit 102. By way of example, nutrients to support the growth of algae can be supplied through the ingress conduit. Aspects of nutrients used to promote growth of algae will be described in greater detail below.

Gas containing carbon dioxide for fixation can also flow into the cultivation tank 104 through a gas-supply conduit 116. The gas can come from a source such as a power generation plant. The gas can include components other than just carbon dioxide. By way of example, the gas can also include nitrogen, carbon monoxide as well as various sulfur ($SO_x$) and nitrogen ($NO_x$) containing compounds. The gas can flow into the system and then into the cultivation tank 104 through a plurality of gas injectors 110. In some embodiments, the gas injectors 110 can be positioned so that the jet of bubbles that they emit causes the liquid medium in the cultivation tank 104 to be turbulent. In some embodiments, the gas injectors 110 can be porous frit-type diffuser plates. In some embodiments, the gas injectors 110 can be positioned so that the bubbles they emit contact the exterior surface of the light transmitting elements 106. For example, the gas injectors 110 can be positioned on the bottom of the light transmitting elements 106. This can be advantageous because the bubbles can serve to create turbulence in the liquid around the exterior surface of the light transmitting elements 106 that will serve to keep the exterior surface relatively clean. Turbulence is also useful in keeping the algae cells in even suspension and insuring periodic movement of algal cells to the illuminated zones near the light transmitting elements 106.

Algae for harvest and some of the spent liquid medium in which it grows can be removed from the cultivation tank 104 through an egress conduit 114. The algae can be separated from the liquid, such as by gravity, centrifugation, or decanting, and then the liquid can be reconstituted and recycled. The algae can then be processed for various purposes. By way of example, in some embodiments, the algae can be processed in order to extract lipids which can then be processed in order to produce commercially valuable compositions. In some cases, the lipids can be subjected to catalytic esterification and transesterification reactions in order to produce an alkyl ester composition such as a biodiesel fuel composition. Exemplary techniques for producing alkyl ester compositions can be found in U.S. patent application Ser. No. 11/833,839, the content of which is herein incorporated by reference. In some cases protein from the algae can be extracted and used for feeding livestock. In some cases carbohydrates (such as cellulose) can be extracted from the algae, hydrolyzed, and then used in a fermentation process for the production of ethanol.

Gases can be vented from the system through a gas release valve 142. In some embodiments, gases can simply be vented into the atmosphere. Because the algae remove carbon dioxide and produce oxygen, the gases being vented will have a lower concentration of carbon dioxide and a higher concentration of oxygen in comparison to the gases entering the cultivation tank 104 through the gas-supply conduit 116. In some embodiments, the gases being vented can be captured and then routed into another algae cultivation tank. For example, the concentration of carbon dioxide in the vented gas can be further reduced by processing in another algae cultivation tank.

While the system shown in FIG. 1 shows carbon dioxide being added to the cultivation system as a gas, it will be appreciated that in some embodiments carbon dioxide can be added as part of an aqueous solution. For example, carbon dioxide can be dissolved in a liquid and then the liquid can be added to the cultivation system. As another example, carbon dioxide can effectively be added to the system as dissolved carbonate or bicarbonate salts. In some embodiments, carbon dioxide can be dissolved in an aqueous nutrient mixture and then added to the cultivation system.

Figure 2:
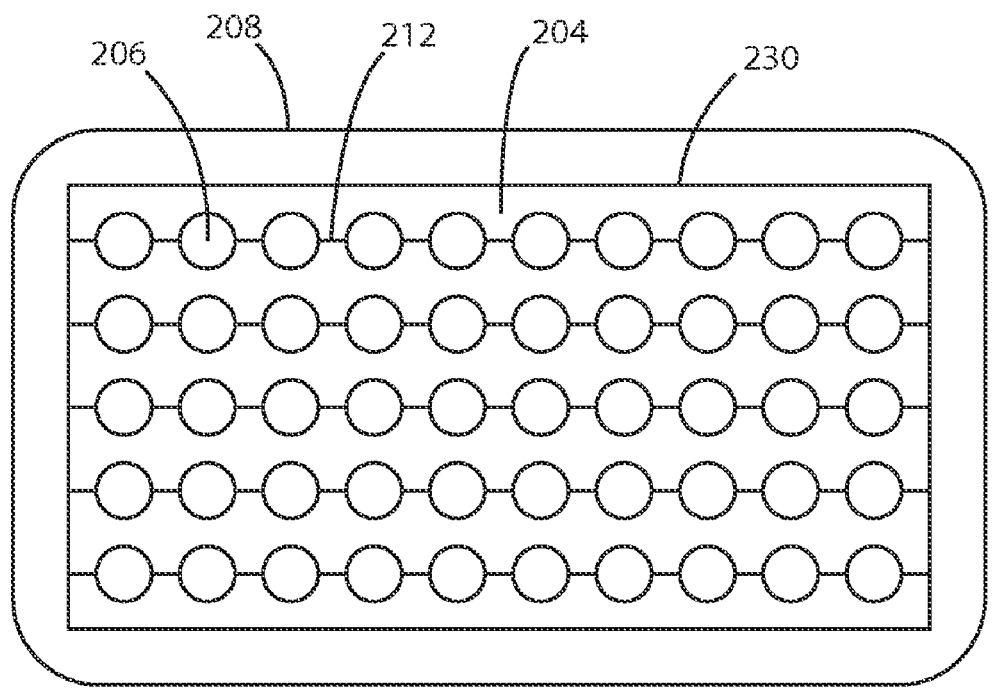
FIG. 2 is a top view of an algae cultivation system in accordance with an embodiment.
Figure 3:
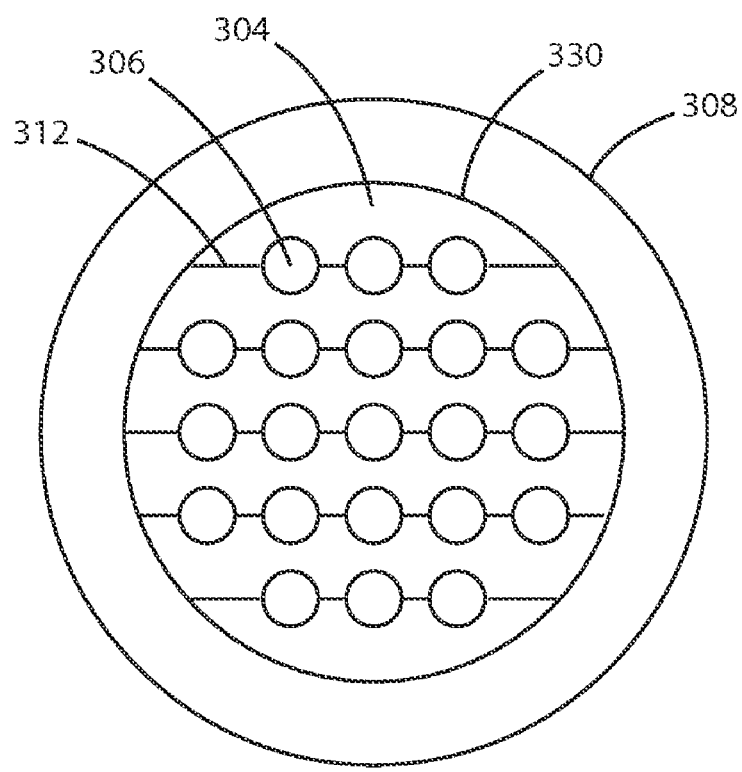
FIG. 3 is a top view of an algae cultivation system in accordance with another embodiment.

The cultivation tank can have many different shapes. For example, FIG. 2 shows a schematic top view of a cultivation system with a cultivation tank 204 having a substantially rectangular shape framed by side walls 230. A plurality of light transmitting elements 206 can be disposed within the cultivation tank and can be supported by a frame 212. The cultivation tank can also include a translucent cover 208. As another example, FIG. 3 shows a schematic top view of a cultivation system with a cultivation tank 304 having a substantially circular shape framed by a side wall 330. A plurality of light transmitting elements 306 can be disposed within the cultivation tank and supported by a frame 312. The cultivation tank can also include a translucent cover 308, such as a rigid or pliable cover.

Figure 4:
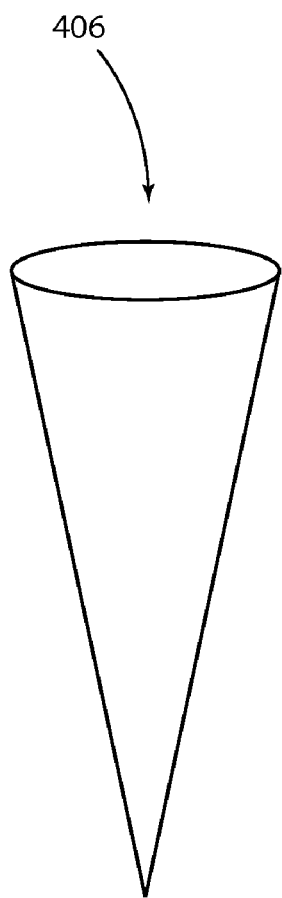
FIG. 4 is a schematic view of a light transmitting element in accordance with an embodiment.

It will be appreciated that light transmitting elements used with various embodiments can take on various shapes. For example, FIG. 4 shows an enlarged view of one exemplary light transmitting element 406. In this embodiment, the light transmitting element 406 has a conical shape. Conical shapes included herein can specifically include frusto-conical shapes. One advantage of a conical shape is that as bubbles are released by a gas injector underneath the cone, the bubbles will follow along with the exterior of the cone on their way to the surface of the liquid medium within the tank.

The light transmitting element 406 can be solid or hollow. Many different materials can be used to construct a light transmitting element 406 including polymers, ceramics, various types of glass, crystal and the like. In some embodiments, the interior of the light transmitting element 406 can include features to enhance the distribution of light throughout the element. By way of example, in some embodiments, the light transmitting element 406 can include optical fibers in order to enhance the distribution of light. In some embodiments, the light transmitting element 406 can include lenses, optical diffusers, and the like.

Figure 5:
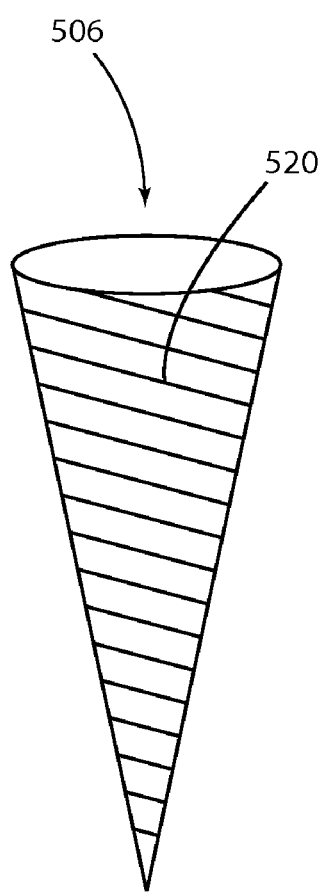
FIG. 5 is a schematic view of a light transmitting element in accordance with another embodiment.

In some cases, the light transmitting element can include surface features that enhance the turbulence generated by air bubbles passing over the exterior surface of the light transmitting element. Referring now to FIG. 5, a schematic view of a light transmitting element 506 is shown in accordance with another embodiment. The light transmitting element 506 includes surface features 520 such as spiral grooves or ridges that function to guide air bubbles around the exterior surface in a swirling pattern. This swirling pattern can serve to enhance light diffraction and scattering in the liquid medium. In some embodiments, transparent colloidal coatings can be applied to the light transmitting elements in order to enhance light scattering and reduce the incidence of wall growth of the algae on the outside of the light transmitting elements.

Figure 6:
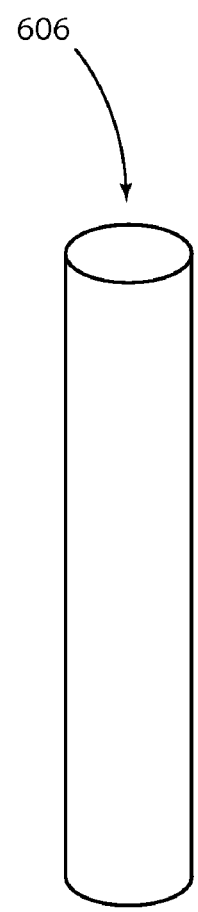
FIG. 6 is a schematic view of a light transmitting element in accordance with another embodiment.

Beyond conical shapes, many other shapes light transmitting elements are contemplated herein. Referring now to FIG. 6, a schematic view of a light transmitting element 606 is shown in accordance with another embodiment. In this embodiment, the light transmitting element 606 has a substantially cylindrical shape.

Figure 7:
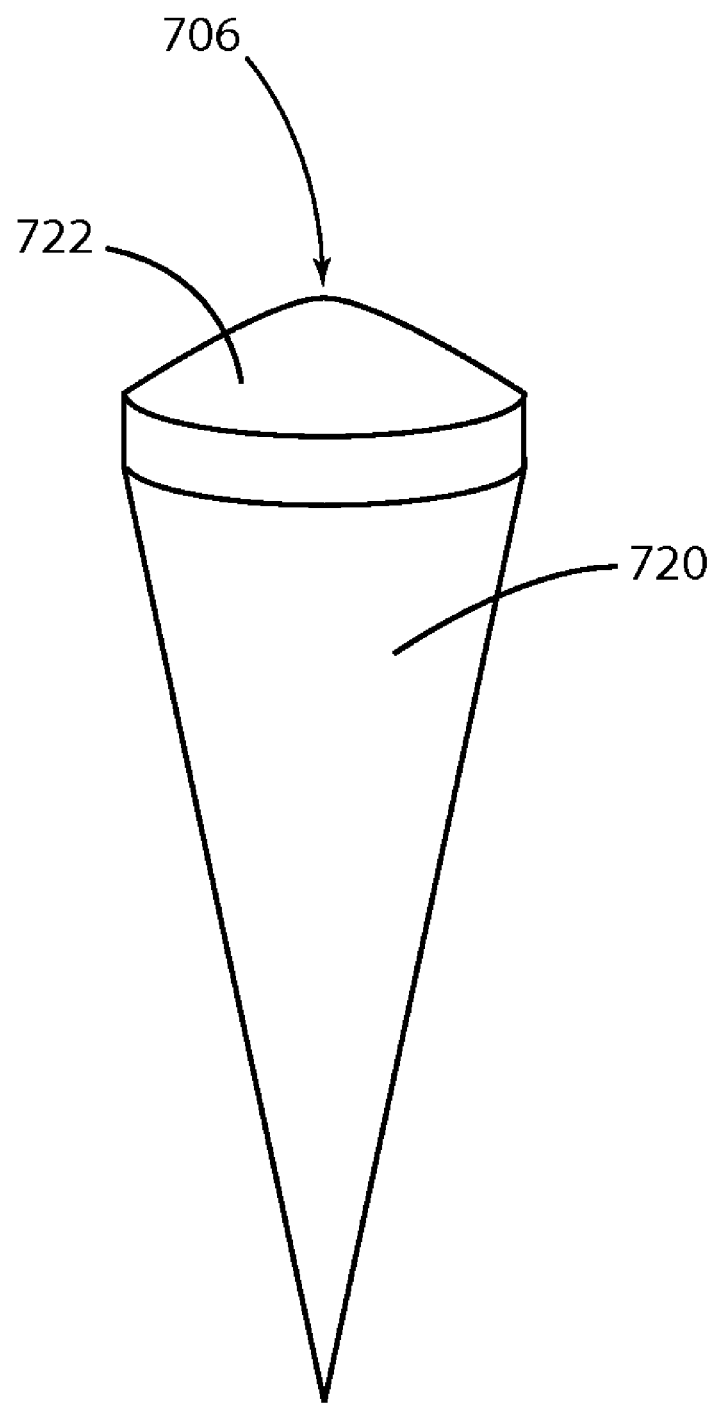
FIG. 7 is a schematic view of a light transmitting element in accordance with another embodiment.

In some embodiments, a light transmitting element can include a light gathering feature in order to enhance the amount of light passing into the light transmitting element from above. By way of example, referring now to FIG. 7, an embodiment of a light transmitting element 706 with a light gathering cap member 722 is shown in accordance with an embodiment. In some embodiments, the cap member 722 can have a convex outer surface that can be effective to gather and focus light into the body 720 of the light transmitting element 706. In some embodiments, the cap member 722 can include a lens. In some embodiments, the cap member 722 can include an anti-reflective coating on its outer surface to reduce reflective losses of light intensity as light enters the cap member 722 from the outside. In some embodiments, the cap member 722 can include a reflective coating on its inner surface (facing the interior of the light transmitting element) to reduce losses of light intensity caused by light traveling back out of the light transmitting element 706 through the cap member 722.

In some embodiments, algae cultivation systems of the invention can include an artificial light source. By way of example, one or more lights can be positioned on the cover, on the light transmitting elements, or in the cultivation tank in order to provide light to the algae within the cultivation tank. This may be desirable to compensate during periods of limited natural light availability, such as during the night, during seasons with fewer hours of natural light, or during cloudy weather patterns. Such lights can include various types of conventional lighting including incandescent lights, fluorescent lights, mercury vapor lights, light emitting diodes, and the like.

Figure 8:
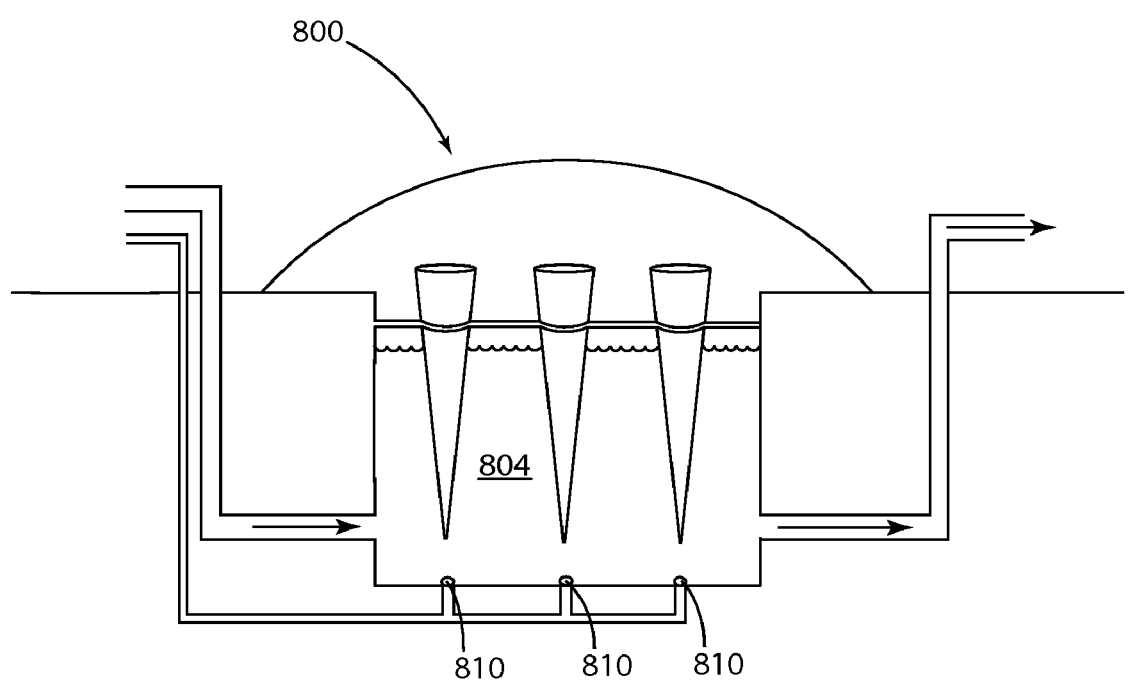
FIG. 8 is a schematic diagram of an algae cultivation system in accordance with an embodiment.

The gas injectors can be positioned in various places within the cultivation tank. In some embodiments, such as that shown in FIG. 1, the gas injectors can actually be attached to the light transmitting elements. However, in other embodiments, the gas injectors can be separate from the light transmitting elements. Referring now to FIG. 8, a schematic view of an algae cultivation system 800 is shown in accordance with an embodiment. In this example, the algae cultivation system 800 includes a cultivation tank 804 with a plurality of gas injectors 810 on the bottom of the cultivation tank 804. In other embodiments, the gas injectors can be positioned, for example, on the side of the cultivation tank 804 or even suspended in middle of the cultivation tank.

Figure 9:
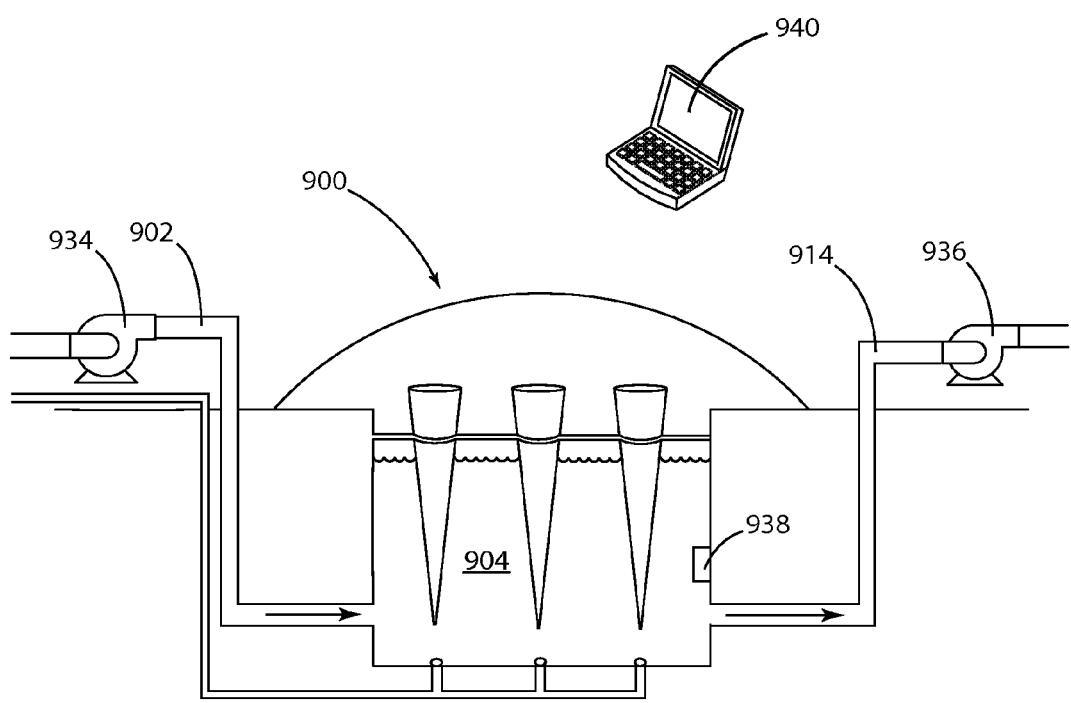
FIG. 9 is a schematic diagram of an algae cultivation system in accordance with another embodiment.

Various operational aspects of algae cultivation systems can be automated in accordance with embodiments herein. Referring now to FIG. 9, a schematic diagram of an algae cultivation system 900 is shown in accordance with another embodiment. In operation, the algae cultivation system 900 may periodically require additional nutrients to foster the continued growth of the algae. In some embodiments, nutrients either be added into the cultivation tank or flow into the cultivation tank through an ingress conduit 902. The flow of liquid through the ingress conduit 902 can be controlled through the use of a first pump 934. The first pump 934 can be in wired or wireless communication with a controller 940 that can operate the first pump 934 as desired including controlling the pumping rate.

Similarly, some of the contents of the cultivation tank will periodically be removed for purposes of harvesting the algae. In some embodiments, the algae can be harvested by withdrawing some of the liquid medium in the cultivation tank through an egress conduit 914. The flow of liquid through the egress conduit 914 can be controlled through the use of a second pump 936. The second pump 936 can be in wired or wireless communication with the controller 940 that can operate the second pump 936 as desired including controlling the pumping rate.

It can be desirable to monitor the conditions within the cultivation tank in order to ensure that optimal growth conditions are maintained. By way of example, it can be desirable to monitor parameters such as temperature, nutrient concentrations, carbon dioxide concentration, pH, and algae population density, amongst others. In some embodiments, the cultivation system 900 can include a sensor module 938 in order to monitor these conditions. It will be appreciated that there are many sensors known to those of skill in the art that can be used in order to measure the aforesaid parameters. By way of example, such sensors can operate using techniques including, but not limited to, optical and/or potentiometric techniques. The sensor module 938 can be in wired or wireless communication with the controller 940. The controller 940 can receive data from the sensor module 938 and use it to appropriately control the operation of the system, including the first pump 934 and the second pump 936 in order to maintain optimal conditions for algae growth.

Cultivation tanks used with embodiments herein can be constructed in various ways. In some embodiments, exemplary cultivation tanks can be constructed above-ground. However, in other embodiments, exemplary cultivation tanks are constructed such that at least a portion of the volume of the cultivation tank is below ground. While not intending to be bound by theory, it is believed that constructing cultivation tanks with at least a portion located below ground can be advantageous at least because the thermal mass of the earth can be used in order to help regulate the temperature of the contents of the cultivation tank. By way of example, in hotter months of the year the thermal mass of the earth may provide a net cooling effect to the contents of the cultivation tank and in colder months of the year the thermal mass of the earth may provide a net warming effect to the contents of the cultivation tank.

Figure 10:
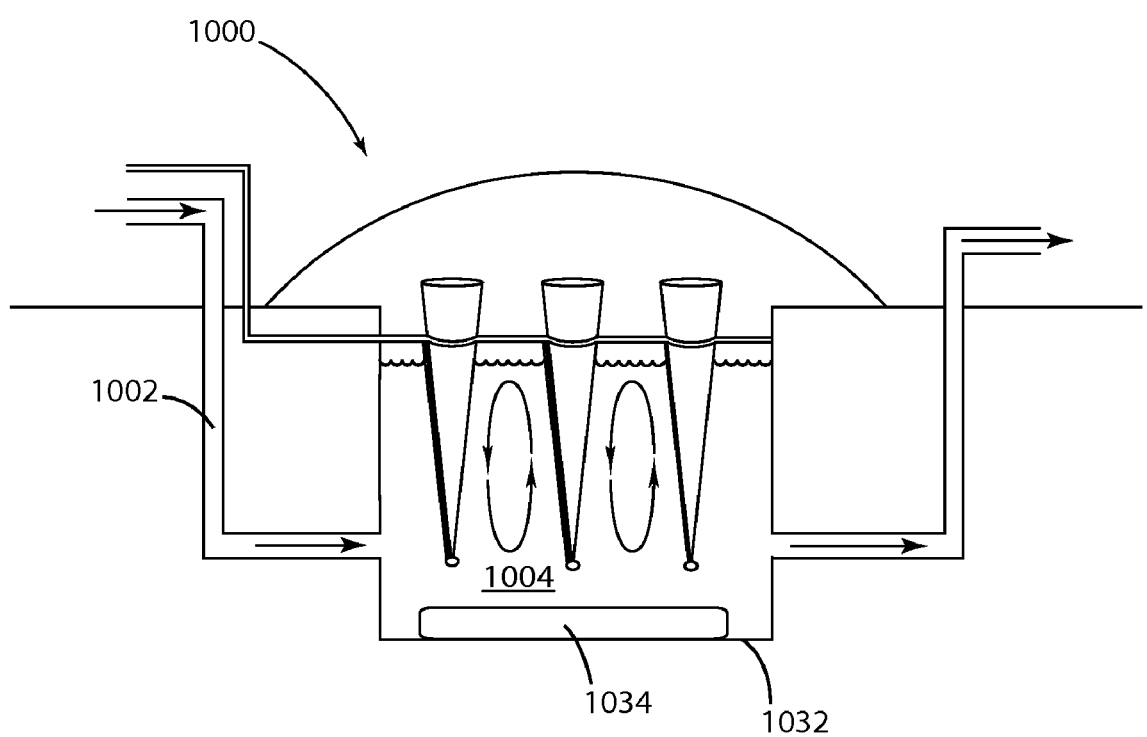
FIG. 10 is a schematic diagram of an algae cultivation system in accordance with another embodiment.

In some embodiments, an active heat control system can be used in order to regulate the temperature of the liquid medium inside of the cultivation tank. Referring now to FIG. 10, a schematic view of an algae cultivation system 1000 including a heat control system 1034 is shown in accordance with an embodiment. In this embodiment, the heat control system 1034 is disposed on the bottom 1032 of the cultivation tank 1004. The heat control system 1034 can be configured to keep the temperature of the liquid medium within the cultivation tank within a desired range. By way of example, the heat control system 1034 can include a heating element, such as a resistive heating element, in order to generate heat. The heat control system 1034 can also be configured to cool the cultivation tank when desired. For example, the heat control system 1034 can be configured to actuate valves and/or a pump to add cooler liquid to the cultivation tank 1004 through an ingress conduit 1002 when desired. In some embodiments, algae cultivation system 1000 can include a heat exchanger system. In some embodiments, heat can be added at the bottom of the cultivation tank and cooler components can be added to the top of the cultivation tank to aide in convection of the system.

In some embodiments, the heat control system 1034 can be configured to maintain the liquid medium in the cultivation tank within a temperature range of between about 50 and about 80 degrees Fahrenheit. However, it will be appreciated that the heat control system 1034 can also be used to maintain the temperature of the cultivation tank within other specific temperature ranges.

As described above, various nutrients may be added to the liquid medium disposed within the cultivation tank in order to foster the continued growth of the algae therein. Such nutrients can be added in dry or liquid forms. In some embodiments, a growth medium such as Bold's Basal Medium can be added in order to support the growth of algae. By way of example, nutrients added to the cultivation tank can include, but are not limited to, urea, $NaNO_3$, $MgSO_4$, $NaCl$, $K_2HPO_4$, $KH_2PO_4$, $CaCl_2$, $ZnSO_4$, $MnCl_2$, $MoO_3$, $CuSO_4$, $CoNO_3$, $H_3BO_3$, EDTA, KOH, $FeSO_4$, and $H_2SO_4$.

Some algal species can switch their metabolism in the dark to grow on organic substrates such as glucose, glycerol, and acetate. This is referred to as heterotrophic growth. As such, some algal species are capable of consuming carbon dioxide both during periods of light and darkness by switching their metabolism. In some embodiments herein heterotrophic algae are used so that the cultivation system can continue to consume gases such as carbon dioxide even in the dark. In such embodiments, nutrients added to the liquid medium can include organic substrates such as glucose, glycerol, and/or acetate in order to support heterotrophic growth.

In addition to nutrients, various other components may be added to the liquid medium within the cultivation tank to maintain operation of the system. By way of example, additional seeding culture samples of algae may be added to the system periodically. Some strains of algae may perform better than others under specific conditions. By way of example, some strains may perform better that others based on specific temperature ranges, the composition of gases entering the system, the amount of light entering the system, etc. The algae culture system can, in effect, be tuned for optimization by the periodic addition of seeding cultures of desirable algae strains.

As shown in example 1 below, the administration of additional light can actually be detrimental the productivity of algal cultures in the absence of sufficient $CO_2$. In some embodiments, the amount of light added can be modulated in order to enhance algal culture productivity. In an embodiment, a method for culturing algae includes measuring the amount of carbon dioxide in a culture system. Specifically, measuring can be performed within a gas supply line that provides carbon dioxide gas to the system and/or measuring can be performed within the cultivation tank of the system. Many different types of carbon dioxide sensors are known in the art and can be used in order to measure carbon dioxide content. The method can also include modulating the amount of light being supplied to the cultivation system based on the measured amount of carbon dioxide. Modulating can include increasing, decreasing, and/or maintaining the amount of light being supplied to the cultivation system. For example, if the system detects that the level of carbon dioxide has fallen below a level necessary for productive algal growth in view of the current amount of light being supplied, the system can decrease the amount of light being supplied. Additionally, if the system detects that the level of carbon dioxide exceeds the amount needed for optimal growth based on the current amount of light being supplied, then the system can increase the amount of light being supplied.

One approach to modulating the amount of light added is to change the ratio of lighted surface area to total algal culture volume. In one embodiment, this can be done by lifting the light transmitting elements at least part way out of the culture medium in the cultivation tank.

Figure 11:
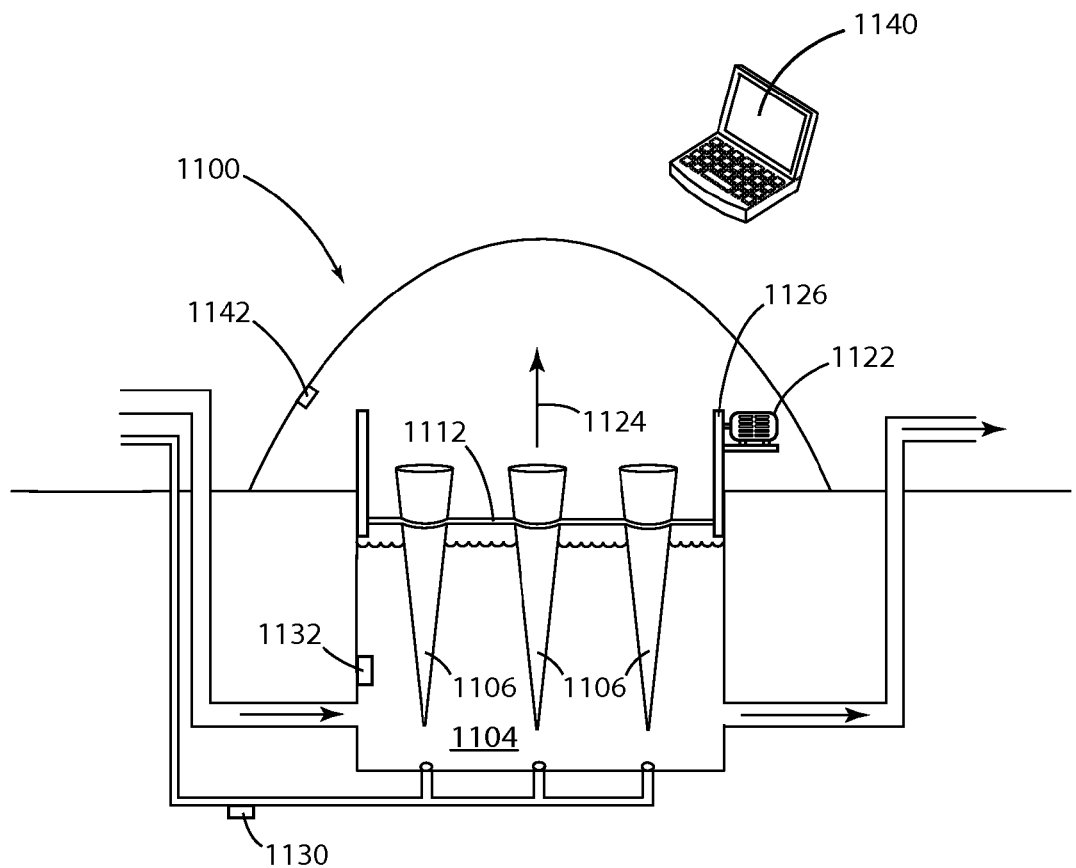
FIG. 11 is a schematic diagram of an algae cultivation system in accordance with another embodiment.

Referring now to FIG. 11 a schematic diagram is shown of an algae cultivation system 1100 in accordance with another embodiment. In this embodiment, light transmitting elements 1106 are held in place with a frame 1112. The frame 1112 can be moved along bracket 1126 by, for example, operating a motor 1122. As the frame 1112 is moved, the light transmitting elements 1106 are moved in direction 1124, out of the tank 1104. In some embodiments, the system 1100 can include carbon dioxide sensors 1130 and/or 1132. Carbon dioxide sensor 1130 can be positioned to measure the carbon dioxide content within an incoming gas line. Carbon dioxide sensor 1132 can be positioned to measure the carbon dioxide content within the cultivation tank 1104. In some embodiments, the system can include a controller 1140 in order to cause the light transmitting elements to be lifted out of the cultivation tank 1104 if the carbon dioxide sensors 1130 or 1132 determine that the carbon dioxide content is below a threshold level, either in the incoming gas line, the cultivation tank 1104, or both. The controller 1140 can receive input from carbon dioxide sensors 1130 and/or 1132, as well as from other sensors that may be included such as light sensor 1142. Exemplary light sensors can include a photoresistor, a charge-coupled device (CCD), a photodiode, a junction field effect transistor (JFET) type optical sensor, or a complementary metal-oxide semiconductor (CMOS) type optical sensor.

Figure 12:
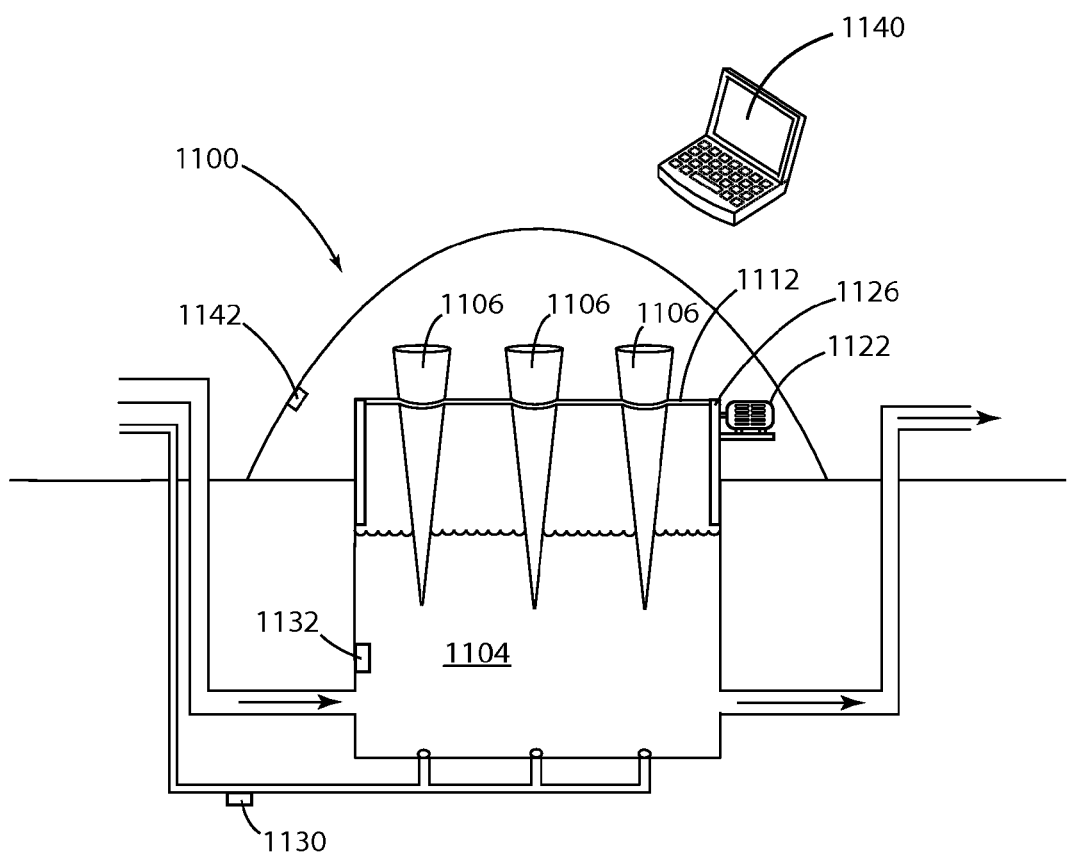
FIG. 12 is a schematic diagram of an algae cultivation system in accordance with another embodiment.

Referring now to FIG. 12, a schematic diagram is shown of the algae cultivation system 1100 with the light transmitting elements 1106 partially lifted out of the cultivation tank 1104. In this view it can be seen that the lighted surface area of the system is now less than when the light transmitting elements 1106 were more fully submerged as shown in FIG. 11.

Another approach to modulating the amount of light added to the system is to change the amount of light passing into the light transmitting elements of the system. By way of example, the light transmitting elements can be fitted with a structure that functions to modulate the amount of light passing into the light transmitting element. It will be appreciated that various structures can be used to modulate the amount of light passing through. By way of example, a controllable filter could be used to modulate the amount of light passing into a light transmitting element. As another example, an iris (diaphragm) or shutter mechanism could be used in order to modulate the amount of light passing into a light transmitting element.

Figure 13:
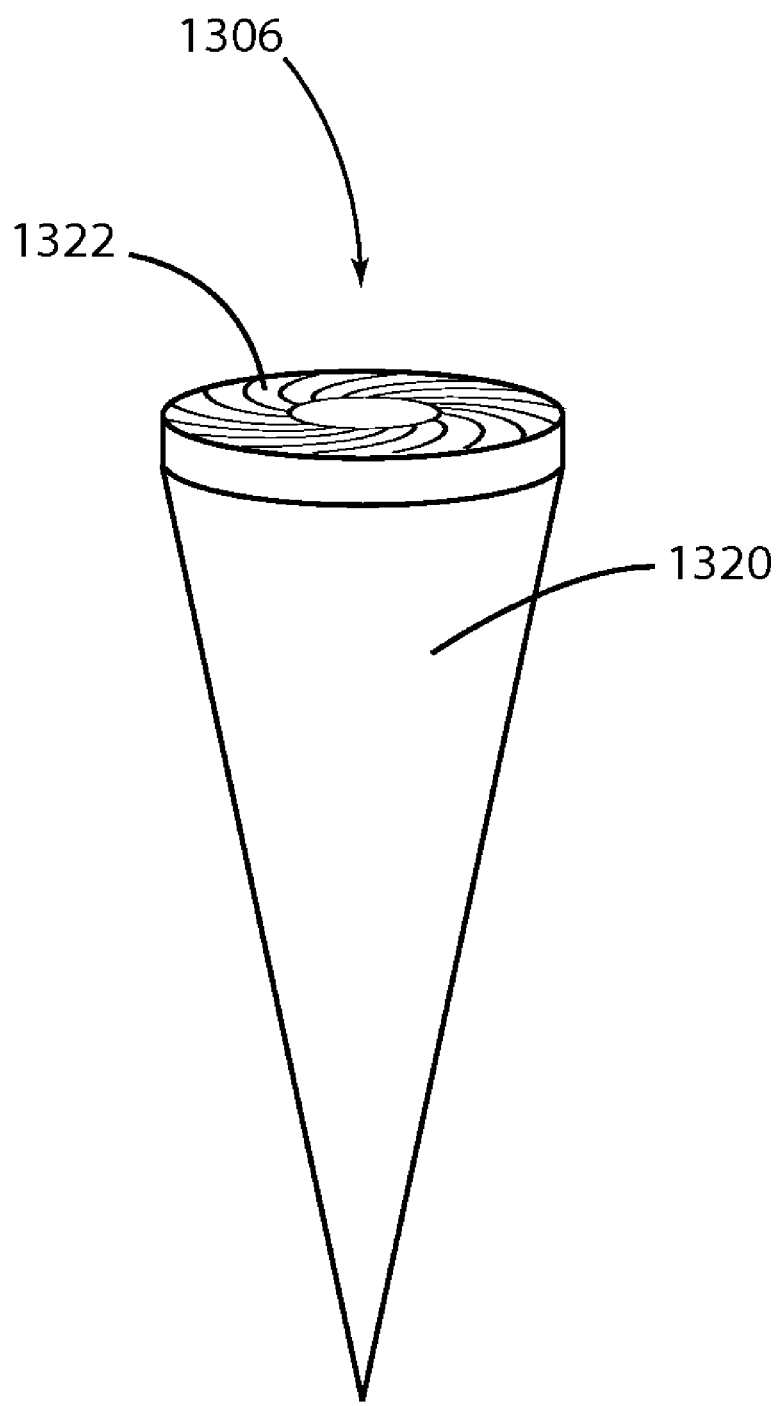
FIG. 13 is a schematic view of a light transmitting element in accordance with another embodiment.

Referring now to FIG. 13, a schematic view of a light transmitting element 1306 is shown in accordance with another embodiment. Light passes through a mechanical iris 1322 mechanism before passing into the body 1320 of the light transmitting element 1306. As such, the mechanical iris 1322 can be actuated in order to modulate (increase or decrease) the amount of light passing into the body 1320 of the light transmitting element 1306.

In some embodiments, the amount of carbon dioxide added to the system can be modulated in order to enhance algal culture productivity. In an embodiment, a method for culturing algae including measuring the amount of light being added to a culture system and then modulating the amount of carbon dioxide input into the system in order to provide optimal algal growth. Many different types of light sensors can be used in order to measure the amount of light being added to a culture system. The light sensor can either be mounted on the inside of the system or the outside of the system. The method can also include modulating the amount of carbon dioxide being supplied to the cultivation system based on the measured amount of light. Modulating can include increasing, decreasing, and/or maintaining the amount of carbon dioxide being supplied to the cultivation system. For example, if the system detects that the level of light exceeds the amount needed for optimal growth based on the current amount of carbon being supplied, then the system can increase the amount of carbon being supplied. The amount of carbon dioxide input into the system can be modulated through actuation of a valve or pump that controls a gas input stream or liquid input stream carrying the carbon dioxide.

In still other embodiments, the amount of light input into the system, the amount of carbon dioxide input into the system, and/or the amount of various nutrients input into the system can all be modulated in order to achieve optimal algal growth.

The present invention may be better understood with reference to the following examples. These examples are intended to be representative of specific embodiments of the invention, and are not intended as limiting the scope of the invention.

EXAMPLES

Example 1

Effect of Various Culture Conditions on Algal Growth

Algae were cultivated in 265 gallon plastic containers. Some containers were used without further modification. Other containers were modified by cutting a series of six, 4 inch holes into the top wall of the plastic container. The holes were spaced 10 inches apart in two rows of three. The holes allowed insertion of clear PVC pipes (3 inch ID×4 feet length) functioning as light transmitting elements. The PVC "light pipes" were capped on the submerged end with 3 inch white PVC plumbing caps. After insertion into the containers the pipes were filled with clear tap water to submerge them in an upright orientation with the open end extending above the top wall of the container. This orientation allowed the pipes to collect and transmit light into the depths of the algae culture contained in the plastic container. Light intensity was measured at various depths within growth medium without algae in both unmodified container and containers with light pipes, as shown in Table 1 below. Submerged light intensity values were determined in uninoculated nutrient solution using a Milwaukee Luxmeter model SM700. The data in Table 1 demonstrates increased light penetration as a result of the insertion of the PVC light pipes into the containers (full sun=108,000 Lux).

TABLE 1

| Liquid Depth (Inches) | Light Intensity (Lux) | |
|---|---|---|
| | Unmodified Container | Container w/ Light Pipes |
| 0 | 61,000 | 65,000 |
| 6 | 15,200 | 20,000 |
| 12 | 13,800 | 19,000 |

TABLE 1-continued

| Liquid Depth (Inches) | Light Intensity (Lux) | |
|---|---|---|
| | Unmodified Container | Container w/ Light Pipes |
| 18 | 13,000 | 17,000 |
| 24 | 12,000 | 15,000 |
| 30 | 11,300 | 13,000 |

Growth of algae was then assessed under various conditions. The conditions tested included: 1.) culture with static (no added gasses) conditions, 2.) culture with air (ambient composition) added at a rate of 700 ml/min (24 hours per day), 3.) culture with 100% carbon dioxide added at a rate of 70 ml/min (added during daylight hours only), 4.) culture with supplemental sunlight via light pipes, and 5.) various combinations of the foregoing.

For all conditions tested, the algae were cultivated under natural sunlight in an outside location that had an unobstructed view of the southern sky. The cultivation period occurred during the months of June through October. During daylight hours, the algal cultures received direct sunlight for approximately 6 hours per day.

To start algal growth, water and Modified Bold's nutrients (Table 2 below) were added to a plastic container to a volume of 250 gallons. A 5% inoculum obtained from a mixed culture of algae maintained in Modified Bold's nutrients was then added. The algal culture was of mixed species composition and was originally obtained from Minnesota lakes. When $CO_2$ was added, it was added at a rate required to maintain the pH of the culture medium near 7.0 or an approximate equivalent of 150 to 300 ppm dissolved carbon dioxide. The pH of the algal cultures varied and was dependent on treatment conditions. Static cultures with active algal growth had an average pH of 10.0. Air treated cultures had an average pH of 9.9. Cultures with added carbon dioxide had an average pH of 7.4.

TABLE 2

| Component | (g/L) |
|---|---|
| $KH_2PO_4$ | 0.175 |
| $CaCl_2$ | 0.019 |
| $MgSO_4\ 7H_2O$ | 0.075 |
| $NaNO_3$ | 0.25 |
| $K_2HPO_4$ | 0.075 |
| NaCl | 0.025 |
| $H_3BO_3$ | 0.00805 |
| $Na_2EDTA$ | 0.01 |
| KOH | 0.0062 |
| $H_3BO_3$ | 0.00286 |
| $FeCl_3\ 6\ H_2O$ | 0.00484 |
| $MnCl_2\ 4H_2O$ | 0.00181 |
| $ZnSO_4\ 7H_2O$ | 0.000222 |
| $NaMoO_4\ 5H_2O$ | 0.00039 |
| $CuSO_4\ 5H_2O$ | 0.00008 |
| $Co(NO_3)_2\ 6H_2O$ | 0.00005 |
| Biotin | 0.0005 |
| $B_{12}$ | 0.0005 |
| Thiamine $B_1$* | 0.1 |

Daily growth of the algae cultures was monitored by measuring the optical density of the algal cultures at a wavelength of 450 nm (Spectronic 20) and by a fluorometric measurement of the in vivo chlorophyll a content of the culture (Aquafluor, Turner Designs, Ex. 460 nm and Em. >665 nm). Cultures were harvested when they reached a target density (O.D. >0.5 and Chlorophyll a >100 µg/l). Cultures were harvested at 10,000×g using an industrial flow through centrifuge with a flow rate of 3 gallons per minute. The harvested algae paste was weighed and the dry matter content was determined using a Mettler-Toledo moisture analyzer, model HR 73.

Figure 14:
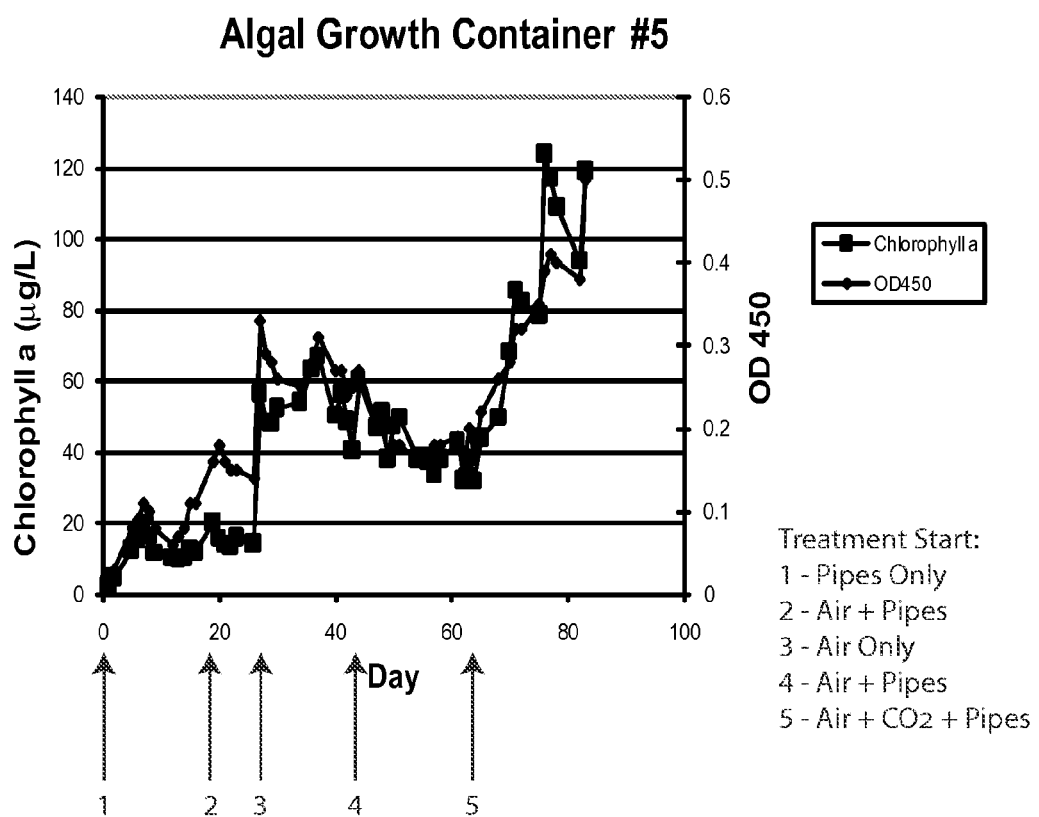
FIG. 14 is a graph of algal growth over time.

Table 3 and FIG. 14 show the growth responses of algae under varying treatment conditions of added air, added carbon dioxide and supplemental light (pipes) within a particular container (#5).

TABLE 3

| | Daily Growth Coefficient | |
|---|---|---|
| Treatment | Δ O.D. | Δ Chlorophyll (µg/l) |
| 1 - Pipes Only | 0.007 | 0.51 |
| 2 - Air + Pipes | 0.005 | 1.00 |
| 3 - Air Only | 0.009 | 2.82 |
| 4 - Air + Pipes | −0.001 | −0.30 |
| 5 - Air + $CO_2$ + Pipes | 0.017 | 5.60 |

Table 4 shows averages across all containers for the treatment conditions of: 1.) static (control), 2.) ambient air only, 3.) ambient air and $CO_2$, and 4.) ambient air, $CO_2$, and light pipes.

TABLE 4

| | Daily Growth Coefficient | | Cell Yield |
|---|---|---|---|
| Treatment | Δ O.D. | Δ Chlorophyll (µg/l) | (g DM/l/d) |
| Static | 0.006 | 1.42 | 0.0041 |
| Air only | 0.010 | 2.95 | 0.0078 |
| Air + CO2 | 0.017 | 4.65 | 0.0086 |
| Air + CO2 + pipes | 0.018 | 5.6 | 0.0096 |

The data show that supplemental light only increased growth when other nutrients most notably carbon dioxide were not limiting. Surprisingly, supplemental light additions when other growth factors, particularly carbon dioxide, were limiting were actually detrimental to growth.

Addition of air to the algal cultures provided limited growth stimulation. This limited stimulatory effect is believed to be a combination of culture agitation which brings algal cells into better illumination periodically, provision of oxygen for the algal cell's respiratory needs and addition of a small amount of carbon dioxide. The addition of supplemental amounts of carbon dioxide further stimulated growth and the best growth rates were achieved when supplemental light was added in combination with air and $CO_2$ additions.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention. As such, it should be understood that many variations and modifications may be made while remaining within the spirit and scope of the invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference of a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, device, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The invention claimed is:

1. An algae cultivation system comprising:
a cultivation tank;
a plurality of light transmitting elements configured to be at least partially submerged in a liquid medium disposed within the cultivation tank, wherein the light transmitting elements increase the effective surface area of the liquid medium exposed to light;
a plurality of gas injectors configured to emit gas into the liquid medium; and
cap members disposed on top of the light transmitting elements, the cap members configured to concentrate light into the body of the light transmitting elements.

2. The algae cultivation system of claim 1, the light transmitting elements comprising a conical shape.

3. The algae cultivation system of claim 1, the light transmitting elements comprising a cylindrical shape.

4. The algae cultivation system of claim 1, the gas injectors positioned so that at least a portion of gas bubbles released from the gas injectors contact an exterior surface of the light transmitting elements after being released from the gas injectors.

5. The algae cultivation system of claim 1, the cultivation tank having a depth of greater than about one foot and less than about twenty feet.

6. The algae cultivation system of claim 1, further comprising a heat control system configured to maintain the liquid medium at a temperature of between about 50 and about 80 degrees Fahrenheit.

7. The algae cultivation system of claim 1, further comprising a translucent cover disposed over the cultivation tank.

8. The algae cultivation system of claim 1, further comprising an ingress conduit in fluid communication with the cultivation tank and an egress conduit in fluid communication with the cultivation tank.

9. The algae cultivation system of claim 8, further comprising a first pump in fluid communication with the ingress conduit and a second pump in fluid communication with the egress conduit.

10. The algae cultivation system of claim 9, further comprising a controller configured to operate the first pump and the second pump.

11. An algae cultivation system comprising:
a cultivation tank;
a plurality of light transmitting elements configured to be at least partially submerged in a liquid medium disposed within the cultivation tank, wherein the light transmitting elements increase the effective surface area of the liquid medium exposed to light;
a plurality of gas injectors configured to emit gas into the liquid medium;
a frame interconnecting a plurality of the light transmitting elements and suspending them within the liquid medium, wherein the frame is configured to move with respect to the cultivation tank in order to lift the light transmitting elements out of the liquid medium; and
a carbon dioxide sensor, the system configured to modulate the amount of light input into the cultivation tank based on data from the carbon dioxide sensor.

12. An algae cultivation system comprising:
a cultivation tank;
a plurality of light transmitting elements configured to be at least partially submerged in a liquid medium disposed within the cultivation tank, wherein the light transmitting elements increase the effective surface area of the liquid medium exposed to light;
a plurality of gas injectors configured to emit gas into the liquid medium; and
an iris mechanism disposed on the light transmitting elements.

13. An algae cultivation system comprising:
a cultivation tank;
a plurality of light transmitting elements configured to be at least partially submerged in a liquid medium disposed within the cultivation tank, wherein the light transmitting elements increase the effective surface area of the liquid medium exposed to light;
a plurality of gas injectors configured to emit gas into the liquid medium; and
a light sensor, the system configured to modulate the amount of carbon dioxide input into the cultivation tank based on data from the light sensor.

14. An algae cultivation system comprising:
a cultivation tank;
a plurality of light transmitting elements configured to be at least partially submerged in a liquid medium disposed within the cultivation tank, wherein the light transmitting elements increase the effective surface area of the liquid medium exposed to light;
a plurality of gas injectors configured to emit gas into the liquid medium; and
the light transmitting elements having an exterior surface comprising surface features configured to increase turbulence in the liquid medium as gas bubbles released from the gas injectors pass by, the surface features comprising a plurality of grooves.

* * * * *